(12) United States Patent
Paroth et al.

(10) Patent No.: US 9,072,551 B2
(45) Date of Patent: Jul. 7, 2015

(54) SURGICAL INSTRUMENT (71) Applicants: Christel Paroth, Tuttlingen (DE); Zbigniew Combrowski, Tuttlingen (DE); Alexander Henninger, Muhlheim (DE)

(72) Inventors: Christel Paroth, Tuttlingen (DE); Zbigniew Combrowski, Tuttlingen (DE); Alexander Henninger, Muhlheim (DE)

( * ) Notice: Subject to any disclaimer, the term of this patent is extended or adjusted under 35 U.S.C. 154(b) by 0 days.

(21) Appl. No.: 14/556,882

(22) Filed: Dec. 1, 2014

(65) Prior Publication Data

US 2015/0088199 A1 Mar. 26, 2015

Related U.S. Application Data (63) Continuation-in-part of application No. 13/489,880, filed on Jun. 6, 2012, now Pat. No. 8,900,280.

(51) Int. Cl.
*A61B 17/04* (2006.01)
*A61B 17/86* (2006.01)
*A61F 2/08* (2006.01)
*A61B 17/70* (2006.01)
*A61B 19/00* (2006.01)

(52) U.S. Cl.
CPC ............ *A61B 17/708* (2013.01); *A61B 17/7085* (2013.01); *A61B 19/30* (2013.01); *A61B 2019/307* (2013.01)

(58) Field of Classification Search
USPC .................................................. 606/308, 319
See application file for complete search history.

(56) References Cited

U.S. PATENT DOCUMENTS

2008/0045953 A1* 2/2008 Garamszegi .................... 606/61
2012/0109224 A1* 5/2012 Biedermann et al. ......... 606/328

* cited by examiner

*Primary Examiner* — Sameh Boles
(74) *Attorney, Agent, or Firm* — Dykema Gossett PLLC (57) ABSTRACT

A surgical instrument includes an implant, which may include a cannulated pedicle screw having a screw head, a tulip connected to the screw head, an extension connected to the tulip, an ini threadedly engaged with at least one of the tulip and the extension, and/or a guide wire disposed in at least one of the extension, the tulip, and the implant.

18 Claims, 7 Drawing Sheets

SURGICAL INSTRUMENT

CROSS-REFERENCE TO RELATED APPLICATIONS

This application is a continuation-in-part application of U.S. patent application Ser. No. 13/489,880, filed Jun. 6, 2012, and additionally claims the benefit of priority to German Application No. 102011050996.8, filed Jun. 9, 2011, both of the aforementioned application being fully incorporated herein by reference as though fully set forth herein.

TECHNICAL FIELD

The invention generally relates to a surgical instrument.

BACKGROUND

The indications for a spondylodesis (stiffening) of the entire spinal column or adjacent vertebrae may be very complex. Stabilizations, for example, may be performed in the case of degenerative change in the spinal column, after tumor removal, infections, or trauma.

In some cases, combinations of dorsal systems (e.g. via rod-pedicle-screw systems) combined with multiple cages for ventral bracing may be used for stabilizing the spinal column.

The statics of the spinal column, which may be a weight-bearing unit, can be compared with those of a crane. The anterior column, which may consist of vertebrae and intervertebral discs, may bear about 80% of the weight and the dorsal structures may bear approximately 20%. From this we can deduct that the anterior portion of the lumbar spine may be primarily subject to compressive forces, while the dorsal portion may be primarily subject to tractive forces. In addition, shearing, torsional, and bending forces may act on both columns.

While the above-mentioned screws/rod-systems may be used in the dorsal area, a cage or implant may be used for ventral bracing.

An objective of the stabilization of the vertebrae may be a quick ossification of the intervertebral space, which may permit lasting freedom from and/or reduction in pain for a patient.

Examples of the indication of a spondylodesis may include unstable vertebral fractures, degenerative instabilities, fractures with sufficient anterior bracing, dislocations, spinal tumors (without anterior defects), and/or prior failed fusion (pseudoarthrosis).

The surgical techniques may be carried out in an open fashion or as minimally invasive procedures, depending on the indication. These procedures may differ in size and type of access or accesses.

Accesses to the affected area can be gained through a combination of a ventral and dorsal access (in case of the cervical spine sometimes ventral only) or through a dorsal, dorsolateral, or lateral access.

An implant of the appropriate dimensions may be chosen depending on the structures and proportions found. Generally, the size may be calculated in such a fashion that the screw reaches into the anterior third of the vertebral body.

Pedicle screws may be screwed into the vertebral body through the pedicle. For safe navigation and guidance, some screws may be cannulated and may be inserted via a guide wire. Some pedicle screws may include additional cross-holes in the thread piece for subsequent cementing.

A rod, which may connect two or more pedicle screw with each other, may be inserted into the head of the screw, which may be called a "tulip". The tulip may be rigid or movable in one or multiple directions, which may facilitate later insertion of the rod.

A rod may be inserted on both sides, and the vertebral bodies to be fixed may then be pressed apart with varying spreading systems, generally via the pedicle screws, to achieve an optimal distance between the vertebral bodies.

During this process, the mobility of the tulip may be obstructive if the objective is to raise vertebral bodies or reconstruct a physiological alignment (e.g., in accident surgery).

Minimally invasive procedures may use an extension of the tulip, which may allow for the extracorporeal, percutaneous insertion of the rod.

Depending on the surgical technique, a variety of a manufacturer's screw forms and associated instrument sets may be used.

It may be disadvantageous to use a variety of different instruments as it may then be necessary for surgeons and surgical assistants to learn and/or remember the specifics of each instrument and screw combination and/or it may be necessary to rely on the manufacturing companies' product managers.

SUMMARY

Embodiments of the present disclosure may provide an improved surgical instrument, which may address some or all of the above-mentioned challenges.

The following features may provide one or more solutions to one or more problems.

A surgical instrument may include a tulip, whereby the tulip features a pressure ring and/or guide element for receiving a pedicle screw. In embodiments, the pressure ring may be arranged on the tulip, in exchangeable fashion.

In embodiments, the guide element(s) may be formed as a single piece on the pressure ring.

In embodiments, the guide element(s) may be separate pieces. It may be advantageous to use one or several pressure rings in combination with one or several guide elements, which may be separate pieces.

In embodiments, both the pressure ring and/or the guide element may be formed as single pieces. This may correspond to the pressure ring being formed as a first component and/or the guide element being formed as a second component.

In embodiments, the pressure ring and/or the guide element may be formed as several pieces. This may include the pressure ring being composed of several individual pieces and/or the guide element being composed of several individual pieces. This may allow for the guide elements or the pressure ring to be inserted into the tulip through recesses/holes. This may be advantageous/beneficial, as it may allow for easy mounting and/or changing of the pressure ring and/or the guide element. For example, the pressure ring may feature an inner and/or outer ring.

In embodiments, the pressure ring and/or the guide element may be twistable, and/or slidable. In embodiments, the pressure ring may formed in such a way that the guide characteristics of the pressure ring may be changed by changing the position of the pressure ring. It may be advantageous for the pressure ring to include one or several guide elements, which may mesh with a screw head, depending on the position of the pressure ring. This may allow for different movements of the screw head or the screw, depending on the position of the pressure ring.

In embodiments, the pressure ring and/or the guide element may feature a shaft. In embodiments, the shaft may be connected to the pressure ring and/or the guide element via a predetermined breaking point, which may make it possible and/or easier to break off the shaft from the tulip. This may create the advantage that the pressure ring and/or guide element can be easily twisted, slid, and/or exchanged.

In embodiments, the pressure ring may include a first guide element, and/or the first guide element may allow for a monoaxial motion of the pedicle screw, relative to the tulip.

In embodiments, the pressure ring may include a second guide element, which may allow a polyaxial motion of the pedicle screw, relative to the tulip.

In embodiments, the pressure ring may include a third guide element, which may be configured to rigidly fix the tulip relative to the pedicle screw (e.g., prevent relative movement).

In embodiments, the pressure ring and/or the guide element may be connected to the tulip as an unitary piece. This may be advantageous because no additional components have to be used.

In embodiments, the guide elements may be connected to the tulip and/or the pressure ring via a predetermined breaking point. This may be advantageous because guide elements that are not desired can be broken off. This may be advantageous because it may make a pressure ring and/or a tulip suitable for rigid, monoaxial, and/or polyaxial bearing of the pedicle screw. In embodiments, the guide elements that are not desired can be broken off at the predetermined breaking points.

In embodiments, the surgical instrument features a tulip extension that may be suitable for connecting with the extension shaft. In embodiments, the design of the extension shaft, the tulip extension, and the tulip may be consistent across one or more of a variety of applications. This may be advantageous because the pedicle screw and the tulip can be exchanged with an extension shaft in easy fashion. This may be advantageous because it may allow a surgeon to always work with his or her familiar/preferred instrument, extension shaft, and/or handle.

In embodiments, the tulip extension may be connected to the tulip via a predetermined breaking point. This may be advantageous because the tulip can be easily disconnected from the extension shaft via the tulip extension. In embodiments, the tulip may be configured such that the tulip, the tulip extension, and the extension shaft comprise a single, unitary piece.

In embodiments, it may be advantageous if the extension shaft at least partially features an extension thread in its anterior area.

In embodiments, the tulip extension may feature a connection thread, at least in its posterior area. In embodiments, the connection thread may be suited to be in an operative connection with the extension thread. This may be advantageous because the extension shaft and the tulip extension can be connected with each other in a simple fashion. In embodiments, the connection thread and/or extension thread may be formed in the opposite rotational direction of the thread of the pedicle screw.

In embodiments, the tulip extension and extension shaft may be formed as individual pieces. In embodiments, the tulip extension may connected to the extension shaft via a predetermined breaking point.

In embodiments, it may be advantageous if the tulip, tulip extension, and extension shaft are formed as individual pieces. In embodiments, the tulip, the tulip extension, and the extension shaft are connected via one or more predetermined breaking points.

In embodiments, the tulip, tulip extension, and extension shaft may be individual pieces, which may be connected with each other via threads, sticks, notches, and/or glue.

In embodiments, the extension shaft may be at least partially hollow. This may be advantageous because this may make the extension shaft suitable for inserting the rod, a screwdriver, an ini, a guide wire, and/or cement into and/or through the extension shaft.

In embodiments, the screwdriver and/or the pedicle screw may be cannulated. This may be advantageous because this may make the components suitable for inserting the guide wire and/or cement. In embodiments, an internal thread or a coupling-like assembly, which may be suitable for docking an instrument or cartridge for cementing, may be located in the cannulation of the pedicle screw.

In embodiments, the fastening of the pedicle screw may happen via the extension shaft with, for example, the counterholder, in which case the screwdriver for the pedicle screw may not be used. In embodiments, it may be desirable to prevent the tulip from rotating during fastening of the pedicle screw, which can be achieved with a relatively simple and/or affordable instrument, such as a cannulated screwdriver.

In embodiments, it may be advantageous if the tulip extension has an internal thread. In embodiments, the surgical instrument may include an ini. In embodiments, the ini may include a large adjustment track. This may be advantageous because an adjustment may be possible with as little as an ini-drive and/or a t-handle, without additional instruments.

In embodiments, the extension shaft and/or the tulip extension may include an exterior cone. In embodiments, the breaking tool may have an inner ring. In embodiments, the inner ring may be formed as a cone. This may be advantageous because it may make the extension shaft also suitable for a procedural step of "breaking." If a breaking tool is positioned on the extension shaft and pressed downward via a lever, the extension shaft may break inwardly at the tulip at the predetermined breaking point. The breaking can also occur laterally or outwardly.

In embodiments, a pedicle screw for a surgical instrument may include a single screw head, which may be brought into operative connection with a first guide element, a second guide element, and/or a third guide element of the pressure rings.

This may be advantageous because embodiments in which no movement, monoaxial movement, or polyaxial movement is desired between tulip and pedicle screw, the same instrument set may be used and only the pressure ring may be exchanged to achieve the desired type of movement, if any. In embodiments, the pressure ring may be attached to the tulip in exchangeable fashion.

In embodiments, the pedicle screw may be cannulated. In embodiments, the pedicle screw may include a self-drilling tip, which may be suitable for opening the pedicle. In embodiments, the pedicle screw may include a self-cutting thread. In embodiments, the pedicle screw may include a partly cylindrical and/or partly conical thread. This may allow for several thread diameters, which may, for example, be connected with each other via conical transitions.

In embodiments, it may be advantageous if one or more pedicle screws includes a multi-functional extension shaft corresponds to a plurality of pedicles screws and each pedicle screw includes a tulip, a tulip extension, and an extension shaft that may be identical for each pedicle screw.

In embodiments, the pedicle screws may be manufactured with different diameters, which may include, for example, about 5 mm, 6 mm, 7 mm, and/or with lengths of about 30 mm to 70 mm. The pedicle screws can be combined with tulips of polyaxial, monoaxial, or rigid design. In embodiments, all pedicle screws may be cannulated, self-cutting, cementable, and/or include diameters of about 6 mm and/or about 7 mm.

In embodiments, the extension shaft may serve as a guide for the rod and rod insertion and, at the same time, may secure (e.g., via an ini) the rod, in pre-assembled fashion.

In embodiments, each step of a procedure, such as screwing the pedicle screws, measuring the length of the rod, cementing if necessary, insertions of the rod, distraction and compression, raising the vertebrae for reconstructing physiological alignment, and/or rod fixation with the ini may be carried out via the extension shaft.

In embodiments, if all rods are fixed in the tulip, the rod inserter may be decoupled from the rod. In embodiments, the extension shaft may then be detached via the SnapOff technique, i.e. the tulip extension from the tulip with the help of an instrument, without burr, extracorporeally.

In embodiments, all pedicle screws can be offered with an integrated ini and drill wire, and/or may be offered in individual and/or sterile packaging.

In embodiments, a small, clearly arranged, instrument set that may be the same for all surgical techniques may feature a drill wire, measuring instruments for the screw length via the drill wire, an instrument combining a thread drill/pedicle opener, a screwdriver/a drive for the ini, a screwdriver/drive for the pedicle screw, a T-handle with ratchet with integrated torque limiter, an instrument for breaking off the tulip/extension shaft, a counterholder and/or an instrument for distraction and compression with rod length measurement.

In embodiments, the predetermined breaking point may be formed as a ring, in one or more pieces. In embodiments, the predetermined breaking point may be formed as several pieces because it may be interrupted by, for example, openings intended for rod insertion and extraction. A predetermined breaking point formed in several pieces can also make it easier to separate the predetermined breaking point.

In embodiments, the pedicle screw, pressure ring, tulip, tulip extension, and the ini may include one or more of a variety of materials, such as, for example, Titanium Grade 5.

In embodiments, manufacturing material for the extension shaft may be stainless steel tubing. In embodiments, the extension shaft can be screw-fastened by positive connection with the tulip extension via a left-hand thread. Additional types of connecting may include soldering, gluing, welding, and plugging.

In embodiments, using the surgical instrument may provide advantages for the surgeon. In embodiments, pre-assembled implants can be used with an ini, the extension shaft can be used in a multifunctional fashion, since it may be configured to serves as a basis for all procedural steps, and/or the system is cementable for open and minimally invasive surgical techniques. In embodiments, a slim, uniform instrument may be provided for all surgical methods. In embodiments, all products may look generally the same and/or may be operated in generally the same manner for monoaxial, polyaxial, and/or rigid pedicle screws. In embodiments, this may allow for few error sources and/or even untrained surgeons may be able to achieve a steep learning curve with such a surgical instrument configuration.

In embodiments, the surgical instrument may be offered in sterile individual packaging. In embodiments, the pedicle screw thread may be formed in a manner that leads to maximal compression.

In embodiments, the tulip or screw head may include formed pockets, which may allow for the pressure rings to be externally and internally switchable or twistable, slidable and pluggable. Formed pockets may allow, prior to sterile packaging and/or before or during the operation, the desired relative movement between tulip and screw head to be set, such as via a pressure ring.

In embodiments, all possible elements between a pressure ring and a screw head, which may provide degrees of freedom for rigid, monoaxial, or polyaxial movement, may be used as guide elements.

In embodiments, a pressure ring may comprise a combination of two pressure rings, for example, or may comprise a pressure ring or pressure rings with another part, which may allow the inner or outer pressure ring to be, if necessary, prior to sterile packaging, before or during the operation (e.g., on a patient), exchanged or selected, to achieve a different screw alignment.

In embodiments, the guide elements and the pressure rings can also be equipped with a breakable shaft with a SnapOff breaking point like the tulip, for the purpose of easy exchanging, twisting, sliding, etc.

BRIEF DESCRIPTION OF THE DRAWINGS

The following briefly describes the embodiments of the present disclosure with help of the enclosed figures. The figures generally illustrate:

FIG. 10 shows an enlarged, cut section of an embodiment of a surgical instrument according to FIG. 1.

DETAILED DESCRIPTION

Figure 1:
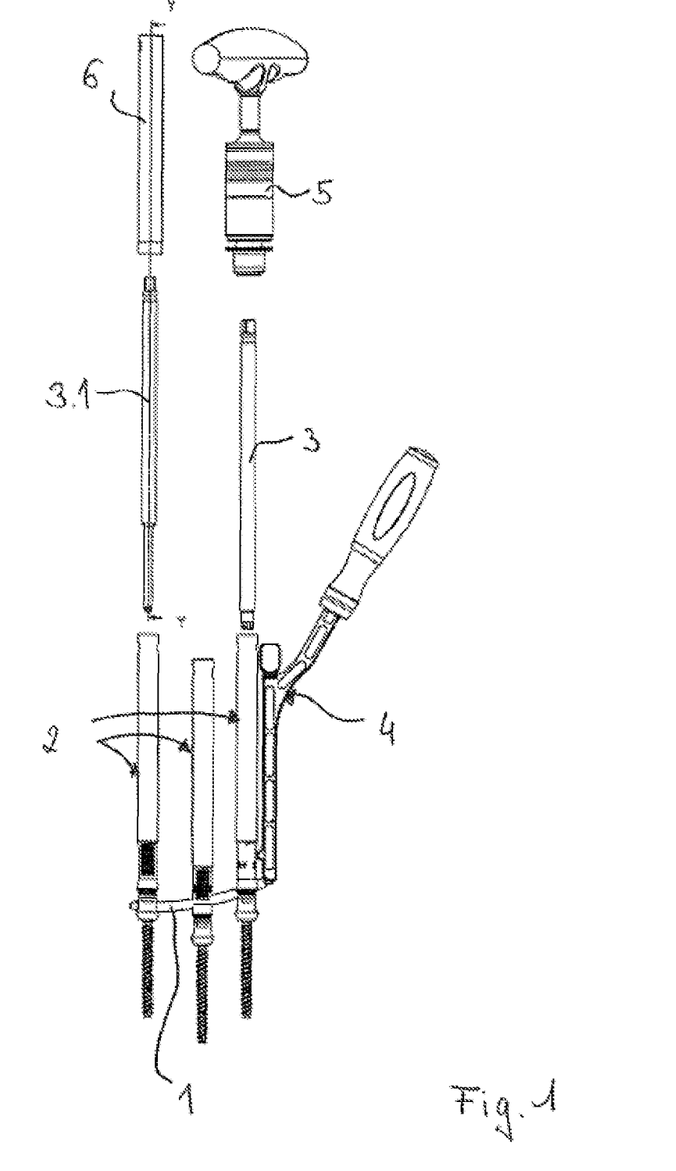
FIG. 1 shows a schematic representation of a set with an embodiment of a surgical instrument, in an implant situation.

Referring to the drawings, FIG. 1 generally illustrates an embodiment of a rod-pedicle screw system for stabilizing the spinal column. In embodiments, a system may include a rod 1, a plurality of implant units 2, a screwdriver 3 for the ini, a collet 4, a T-handle 5 with torque limiter, and/or a breaking sleeve 6. In embodiments, screwdriver 3, collet 4, and/or T-handle 5 may be used with some or all of screw units 2.

In FIG. 1, an embodiment of a screwdriver 3.1 for an implant 7 is also represented.

Figure 2:
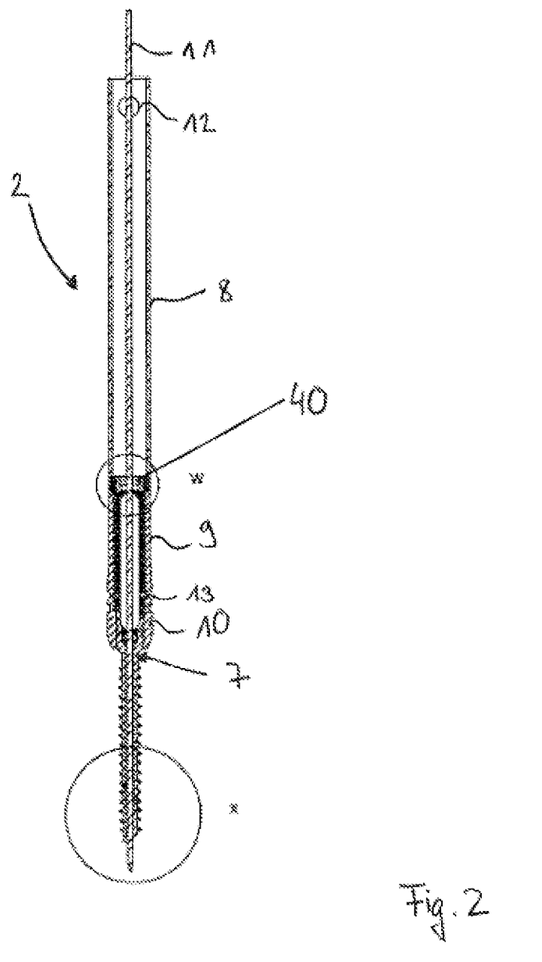
FIG. 2 shows a sectional representation of an embodiment of a surgical instrument.

FIG. 2 shows an enlarged sectional representation of an embodiment of an implant unit 2. In embodiments, an implant unit 2 may include an implant 7, an extension shaft 8, a tulip extension 9, and/or a tulip 10. In embodiments, an implant unit 2 may comprise a screw unit and/or may be referred to herein as screw unit 2. In embodiments, implant 7 may comprise a pedicle screw and/or may be referred to herein as pedicle screw 7; however, it should be understood that implant 7 is not limited to a pedicle screw.

In embodiments, the extension shaft 8, the tulip extension 9, the tulip 10, and the pedicle screw 7 are cannulated. In embodiments, a guide wire 11 may be inserted into the components. In embodiments, the extension shaft 8 may have an opening 12 in an upper area, that may be configured for counterholding.

Figure 3:
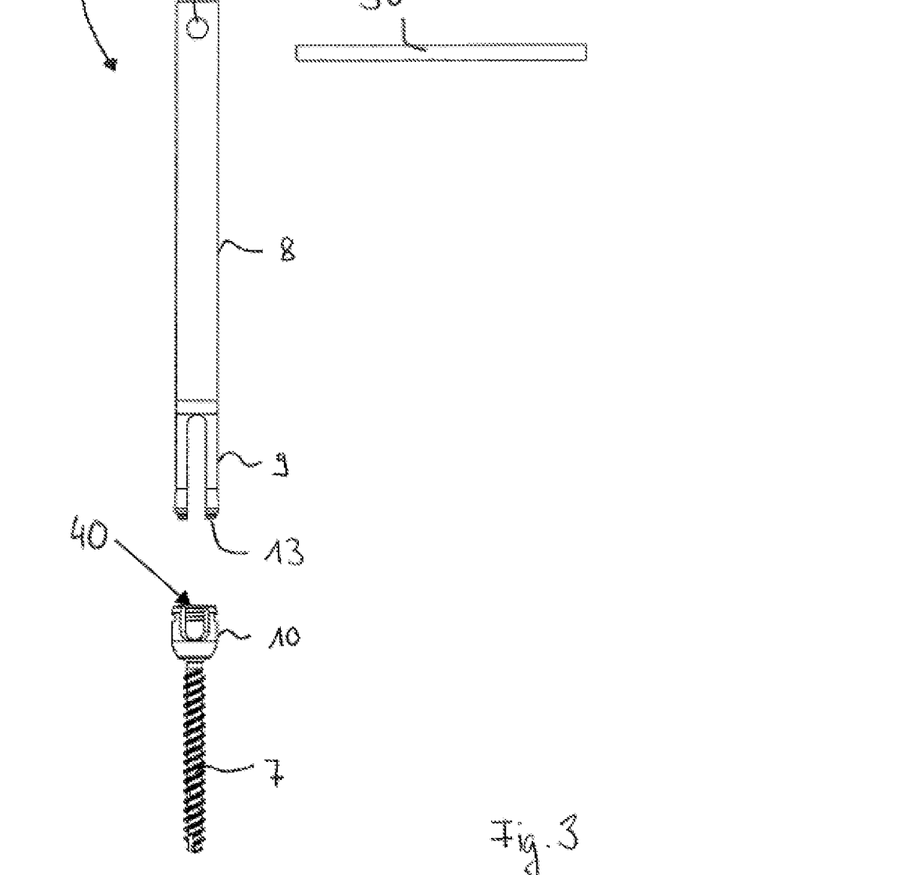
FIG. 3 shows a lateral view of an embodiment of a surgical instrument, in which the instrument is separated at the predetermined breaking point.

In embodiments, tulip extension 9 and the tulip 10 may be connected to each other via a predetermined breaking point 13. FIG. 3 generally shows an embodiment of the screw unit 2, in which the tulip extension 9 and the tulip 10 may be separated at the predetermined breaking point 13.

Figure 4:
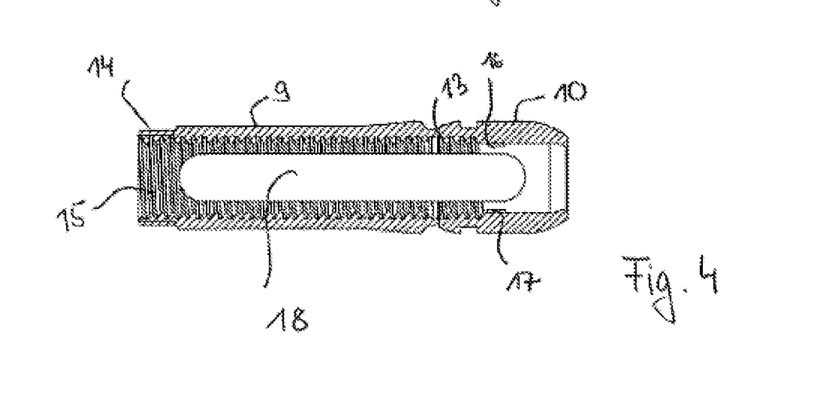
FIG. 4 shows a schematic representation of an enlarged, cut section of an embodiment of an instrument.

FIG. 4 generally shows an enlarged sectional representation of an embodiment of the tulip extension 9 with the tulip 10, which may be connected at the predetermined breaking point 13. The tulip extension 9 features a connection thread 14 at an exterior surface of a posterior area. Furthermore, in embodiments, the tulip extension 9 may include an inner thread 15 on its interior surface. In embodiments, the connection thread 14 may be a left-hand thread. In embodiments, the inner thread 15 may be a right-hand thread. The inner thread 15 reaches into an upper area of the interior surface of the tulip 10.

In embodiments, the tulip 10 may include two retaining collars 16 and 17 on each interior surface, approximately at medium height. In embodiments, an oblong hole 18 may be drilled into the tulip extension 9 and the tulip 10, and oblong hole 18 may be suitable for receiving the rod 1.

Figures 5, 6, 7, 8, 9:
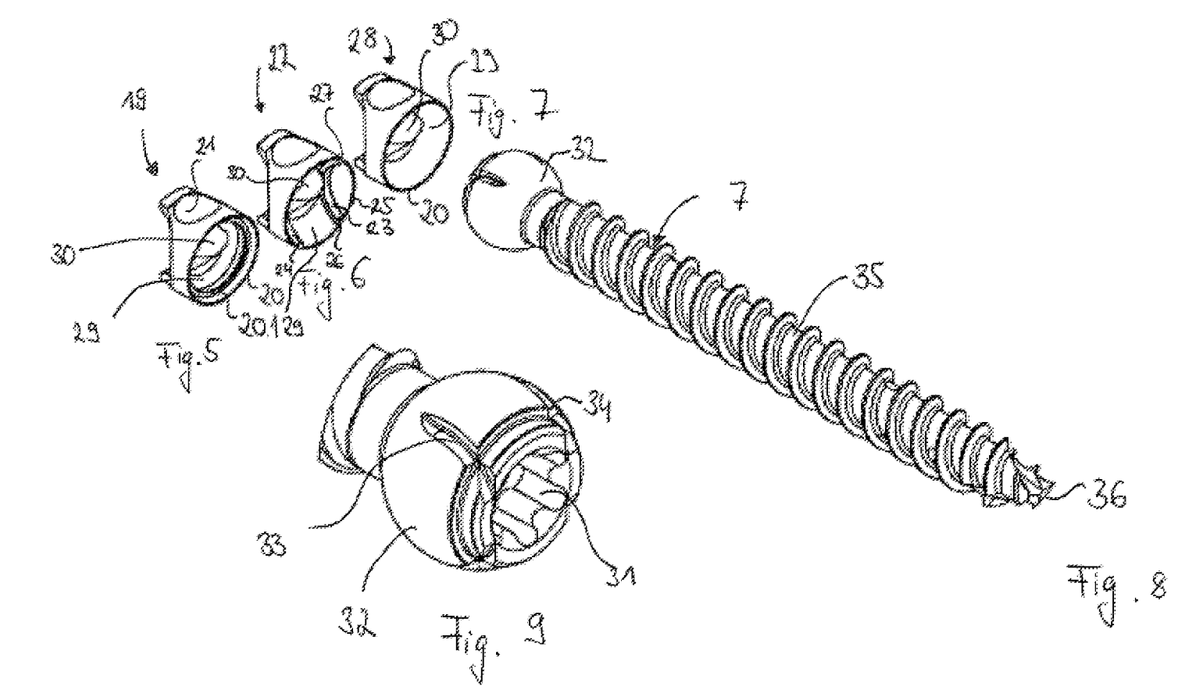
FIGS. 5 to 7 show different embodiments of design examples of a pressure ring for an inventive surgical instrument.
FIG. 8 shows a schematic representation of a pedicle screw for an embodiment of a surgical instrument, in perspective view.
FIG. 9 shows the enlarged representation of a pedicles screw head, in perspective view.
Figure 11:
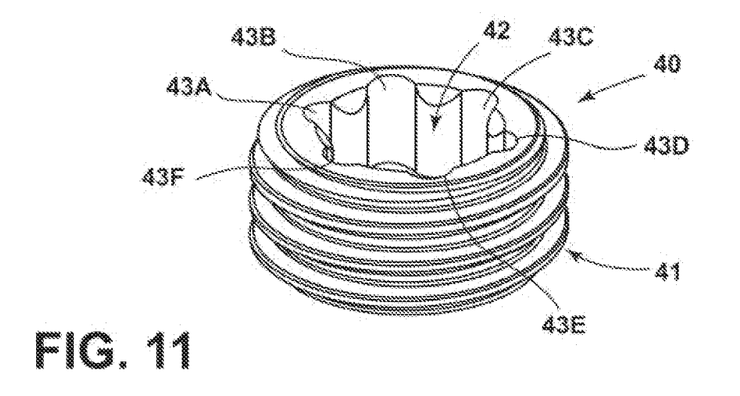
FIG. 11 generally shows an embodiment of an ini in accordance with teachings of the present disclosure, in side view.
Figure 12:
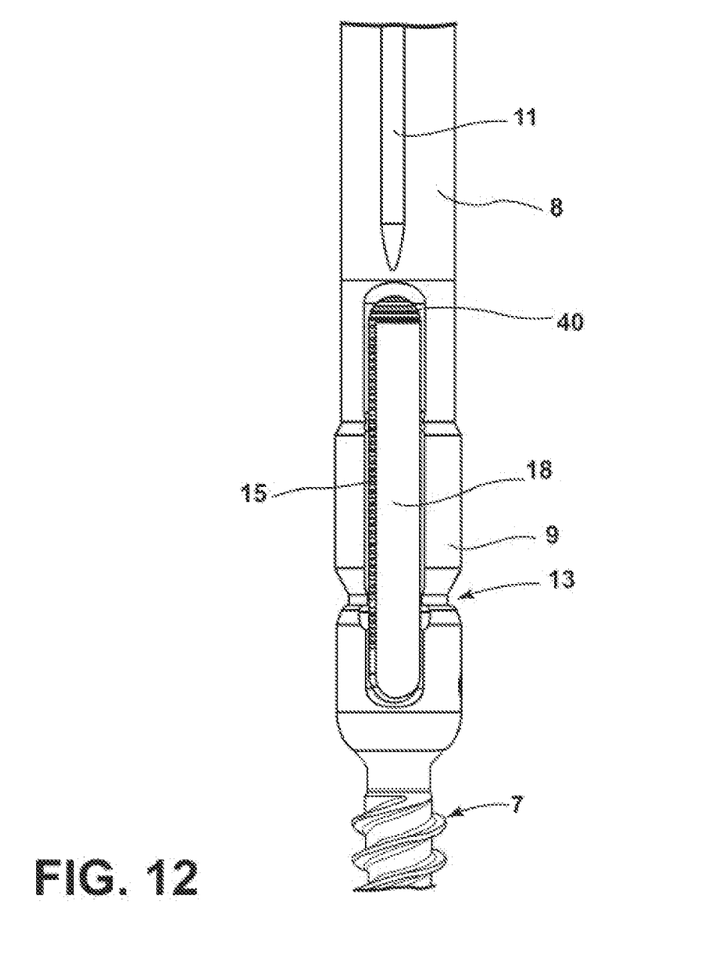
FIG. 12 generally shows portions of an embodiment of a surgical instrument and a pedicle screw in accordance with teachings of the present disclosure, in perspective view.
Figure 13:
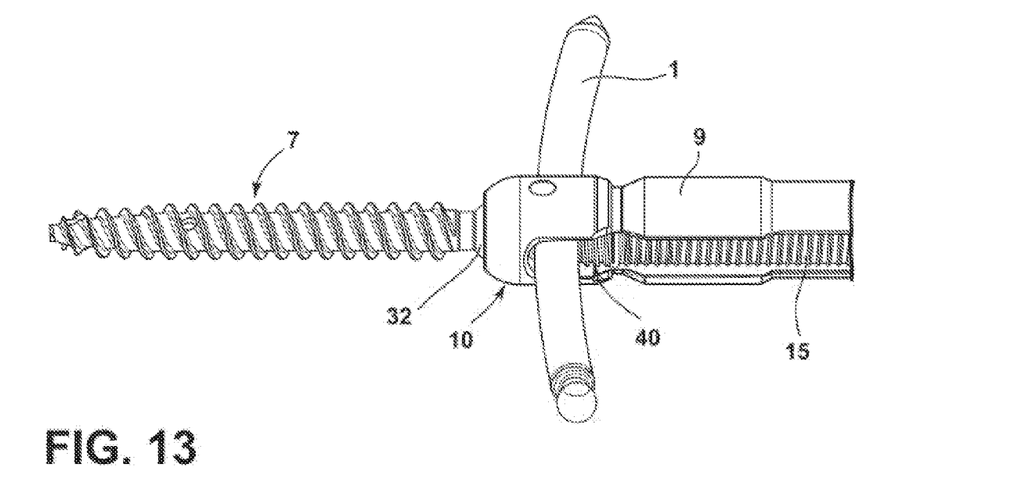
FIG. 13 generally shows portions of an embodiment of a surgical instrument and a pedicle screw in accordance with teachings of the present disclosure, in perspective view.
Figure 14:
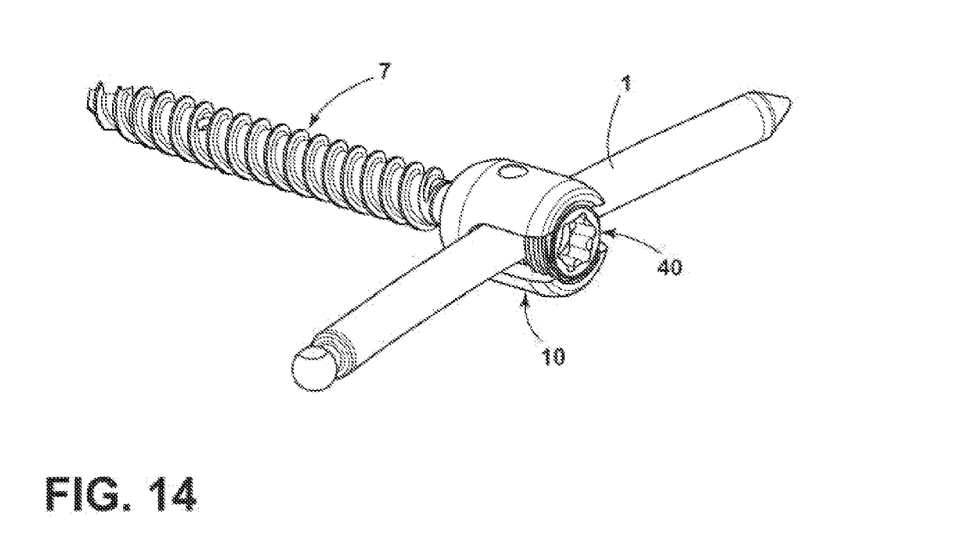
FIG. 14 generally shows portions of an embodiment of a surgical instrument and a pedicle screw in accordance with teachings of the present disclosure, in perspective view.

FIG. 5 shows an embodiment of a pressure ring 19. The pressure ring 19 may include a half-shell-formed interior surface 29 with an opening 20. The pressure ring 19 may be suitable for rigidly holding a pedicle screw 7. For this purpose, the pressure ring 19 may include a circumferential notch 20.1 on its interior surface 29, and circumferential notch 20.1 may be configured to serve as a guide element. For the purpose of fixing the pressure ring 19 in the tulip 10, the pressure ring 19 may include a recess 21, which the retaining collar 16 of the tulip 10 may grip, such as represented in FIG. 4. Opposite to the recess 21, the pressure ring 19 may include another recess that is not represented, which can be operatively connected with the retaining collar 17.

FIG. 6 shows another embodiment of a pressure ring 22, suitable for monoaxial holding of the pedicle screw 7. Pressure ring 22 may essentially be formed analogous to pressure ring 19. Pressure ring 19 may include a half-shell-formed interior surface 29 with an opening 20. The pressure ring 19 and the pressure ring 22 may differ in the shape of the guide element. For example, and without limitation, as a guide element, the pressure ring 22 may include a first bridge 23 and a second bridge 24. The bridges 23 and 24 may essentially be arranged in symmetrical fashion. The bridge 23 may include a semicircular arch-shaped form. The bridge 23 may be fastened to an interior surface 29 of the pressure ring 22, in such a fashion that the ends of the semicircular arch 26 and 27 may end at one edge 25 of the pressure ring 22. The edge 25 may be the edge, which may faces the pedicle screw 7 at mounted screw unit 2.

FIG. 7 shows another embodiment of a pressure ring 28. In embodiments, the pressure ring 28 is may essentially be formed analogous to the pressure rings of the previous design examples (e.g., pressure ring 19 and/or pressure ring 22), but may include a guide element with a different configuration. In embodiments, the pressure ring 28 may allow for a polyaxial relative motion of the pedicle screw 7 relative to the tulip 10. For this, an interior surface 29 of the pressure ring 28 may be formed as half-shell. In embodiments, the half-shell may feature a hole 30 that may be directed upwards.

In embodiments, the hole 30 in the half-shell 29 may serve for using a polygon socket 31 in a screw head 32 of the pedicle screw 7, such as represented in FIG. 9.

In embodiments, as generally illustrated in the enlarged representation of the screw head 32 in FIG. 9, the screw head 32 may include guide elements, as well, which may interact with the pressure rings 19, 22, and 28.

In embodiments, all pressure rings 19, 22, and 28 may be configured for use with respective pedicle screws 7 that each include a screw head 32 with generally the same form. In embodiments, the screw head 32 may include a ball-shaped form, which may allow it to interact with the half-shell-formed interior surface 29 of the pressure rings 19, 22, and/or 28 like a ball joint.

In embodiments, the screw head 32 may include two grooves 33 and 34. The grooves 33 and 34 may be formed as recesses on the screw head 32. The grooves 33 and 34 may essentially be formed symmetrically. The grooves 33 and 34 may run as half-circular arcs on lateral areas of the screw head 32, which may be ball-shaped. In embodiments, the grooves 33 and 34 may be positioned in such a way that they run onto the bridges 23 and 24 of the pressure ring 22. This may allow for a monoaxial motion.

In embodiments, the pedicle screw 7 may feature a thread at its pedicle screw shaft 35. The thread may be double-threaded, self-drilling, and/or self-cutting.

In embodiments, a tip 36 of the pedicle screw shaft 35 may be self-cutting and/or self-drilling. In embodiments, the pedicle screw shaft 35 may be cone-formed, so that the pedicle screw shaft 35 may include a smaller diameter at an anterior area of the tip 36 than in a posterior area (e.g., close to the screw head 32).

In embodiments, the pedicle screw 7 may be cannulated, such as generally illustrated in FIG. 2, for example. This may have the advantage that, for example, a guide wire 11 may be inserted through the pedicle screw 7 and/or the pedicle screw 7 may, additionally or alternatively, be suitable for introducing cement. In embodiments, a guide wire 11 may be inserted though extension shaft 8, tulip extension 9, tulip 10, ini 40, and/or pedicle screw 7. In embodiments, the pedicle screw 7 may include continuous holes in its pedicle screw shaft 35, through which the cement, which may be introduced through the cannula of the pedicle screw 7, may flow outwardly into the vertebral body and may be able to join with the vertebral body.

FIG. 10 generally shows a cut and enlarged section of an embodiment of a screw unit 2 with part of an embodiment of the rod 1 according to FIG. 1. In embodiments, the pedicle screw 7 with the pedicle screw head 32 may be inside the tulip 10. One of the pressure rings 19, 22, or 28 may be inserted into the tulip 10 and may allow for the desired movement of the pedicle screw 7.

Embodiments of the present disclosure may include one or more functionalities.

For example, and without limitation, the screw elements 2 can be used in open or minimally invasive fashion, depending on indication. After determining the implant dimensions, the correct position for the pedicle screw 7 may be identified, which may be via an x-ray mode with a Jamshidi-needle or the guide wire 11.

Subsequently, in embodiments, the guide wire 11 and/or a portal may be used. For controlling the pedicle screw length, in embodiments, additional measuring instruments can be used via the guide wire 11 to determine or compare the screw length.

In embodiments, the opening of the pedicle and the cutting of the thread may happen directly with a self-cutting thread of the pedicle screw 7 at the pedicle screw shaft 35. A cannulated pedicle screw 7 may contain a polygon socket 31 in screw head 32, which may be torx-like, and the cannulated pedicle screw 7 may be securely inserted and screwed into the vertebral body and/or through the pedicle via the guide wire 11.

In embodiments, in the case of brittle, hard bones or brittle bone disease, the opening of a pedicle and the thread cutting may be done with a combination instrument. In embodiments, different designs of a thread drill may be used.

In embodiments, in cases of a lack of compression or osteoporotic vertebral bodies, cement may be inserted through the cannulated pedicle screw 7, such as after the cannulated pedicle screw 7 is screwed into place.

In embodiments, during percutaneous inserting of the rod 1, the rod 1 may be inserted from above through the extension shaft 8 and may once again be extracted from one side through the oblong hole 18 in the tulip extension 9 or the tulip 10 and/or guided through the vertebral body. This may allow for connecting two or more vertebral bodies with each other. In embodiments, a rod 1 may include lengths up to or larger than approx. 120 mm.

In embodiments, a next step may include distraction or compression, which may be accomplished via the extension shaft 8, in extracorporeal fashion. Additionally or alternatively, vertebral bodies may be raised to reconstruct a physiological alignment.

In embodiments, distraction or compression may be achieved with the help of an instrument, which is adjustable alongside the extension shaft 8. This instrument may also serve to determine the length of the rod 1.

In embodiments, raising of vertebral bodies may happen via only the pre-assembled ini 40, an ini-drive 3, and a T-handle 5, without additional instruments. In embodiments, a pre-assembled ini 40 may include a large adjustment track.

In embodiments, if all rods 1 are fixed in the tulips 10 of the screw units 2 and tightened to the specified torque, the extension shaft 8 can be broken off at the predetermined breaking point 13. Predetermined breaking 13 point may correspond to a so-called SnapOff-connection. In embodiments, extension shaft 8 and/or tulip extension 9 may be broken off from tulip 10 via a non-represented instrument and/or without leaving any burrs. Additionally or alternatively, a breaking sleeve 6 may facilitate breaking extension shaft 8 and/or tulip extension 9 off from tulip 10 (e.g., at predetermined breaking point 13), which may be accomplished extracoroporeally. Breaking sleeve 6 may be configured (e.g., have a larger internal diameter than) to slide over and/or may be disposed around extension shaft 8 and/or tulip extension 9.

In embodiments, a tulip extension shaft breaking tool may be used in extracorporeal fashion.

In embodiments, a counterholder 50 can be put on the extension shaft 8, in extracorporeal fashion. Counterholder 50 may be configured to prevent rotation of extension shaft, tulip extension 9, and/or tulip 10, such as during driving pedicle screw 7 and/or tightening of the ini 40 to the specified torque. In embodiments, the extension shaft 8 may feature an opening 12 to connect to counterholder 50.

In embodiments, the extension shaft 8 may have an external cone, which may be disposed above the predetermined breaking point 13 on the tulip extension 9. In embodiments, the breaking tool may feature an inner ring, which may be cone-formed. In embodiments, if the breaking tool is put on extension shaft 8 and, for example, pressed down via a non-represented lever, the extension shaft 8 may break off inwardly at the tulip 10 at the predetermined breaking point 13. In embodiments, breaking off extension shaft 8 from the tulip 10 can also happen outwardly or laterally, however. For this purpose, an instrument can be used, which may partially cut or crop at the predetermined breaking point 13.

In embodiments, if the rods 1 have been tightened to the specified torque, the rod inserter can be decoupled from the rod 1 and/or removed from the body.

In embodiments, as generally illustrated in FIGS. 11-14, an ini 40 may be configured such that it generally resembles a set screw and/or a locking screw. In embodiments, an ini 40 may include an external thread 41 that may be configured for engagement with internal threads of tulip 10. In embodiments, an ini 40 may be cannulated and/or include an aperture 42 extending at least partially through the body of ini 40. Aperture 42 may include a generally polygonal shape and/or may be similar to that of polygonal socket 31 of screw head 32. Aperture 42 may include one or more recesses 43A, 43B, 43C, 43D, 43E, 43F that may be disposed about a circumference of aperture. Recesses 43A-43F may be generally rounded and/or may be spaced generally evenly or unevenly about the circumference of aperture 42. Aperture 42 and/or recesses may be configured to cooperate with and/or engage screwdriver 3, which may include a corresponding polygonal pattern. In embodiments, a minimum diameter of aperture 42 may be at least as large or larger than a diameter of screwdriver 3.1, which may allow screwdriver 3.1 to be inserted through ini 40 and/or rotate pedicle screw 7 via polygonal socket 31 without rotating ini 40.

In embodiments, an ini 40 may be provided in a preassembled configuration. A preassembled configuration may include an implant 7 being disposed at least partially in and/or connected to tulip 10. In embodiments, an implant may include, for example and without limitation, a pedicle screw. Ini 40 may disposed in and/or threadedly engaged with one or more of extension shaft 8, tulip extension 9, and tulip 10. Tulip 10 may be connected to extension tulip extension 9 at breaking point 13 (e.g., tulip 10 may not yet have been broken off from tulip extension 9). Guide wire 11 may be inserted through and/or disposed in extension shaft 8, tulip extension 9, tulip 10, ini 40, a pressure ring (e.g., pressure ring 19, 22, and/or 28), and/or pedicle screw 7. In embodiments, a breaking sleeve 6 may be disposed around extension shaft 8 and/or tulip extension 9. In embodiments, an pedicle screwdriver 3.1 may be configured to extend through and/or may be disposed in extension shaft 8, tulip extension 9, tulip 10, ini 40, and/or a pressure ring (e.g., pressure ring 19, 22, and/or 28), to drive pedicle screw 7. In embodiments, an ini screwdriver 3 may be configured to extend through and/or may be disposed in extension shaft 8 and/or tulip extension 9 to drive ini 40. In embodiments, a T-handle may include an integrated torque limiter and/or may be configured to drive ini screwdriver 3.

In embodiments, a preassembled configuration may include a first exchangeable pressure ring (e.g., pressure rings 19, 22, 28) disposed at least partially between screw head 32 and tulip 10. In embodiments, the first exchangeable pressure ring may permit a first type of movement (e.g., monoaxial, polyaxial, no movement) between pedicle screw 7 and tulip 10. First exchangeable pressure ring may be exchangeable with a second exchangeable pressure ring and/or the second exchangeable pressure ring may permit a second type of movement that may be different from the first type of movement. In embodiments, the second type of movement may include substantially no movement between the tulip and the pedicle screw (e.g., the second exchangeable pressure ring may prevent movement between pedicle screw 7 and tulip 10). In embodiments, the pressure rings may be exchanged during an operation on a patient.

The foregoing descriptions of specific embodiments of the present disclosure have been presented for purposes of illustration and description. They are not intended to be exhaustive or to limit the invention to the precise forms disclosed, and various modifications and variations are possible in light of the above teaching. It should be understood that references to a single element are also intended to include embodiments that may include more than one of that element or zero of that element. It should also be understood that references to directions, such as vertical, horizontal, top, bottom, are provided for illustrative purposes only and are not intended to limit the scope of the disclosure.

The embodiments were chosen and described in order to explain principles of the invention and its practical applications, to thereby enable others skilled in the art to utilize the invention and various embodiments with various modifications as are suited to the particular use contemplated. It is intended that the scope of the invention be defined by the claims and their equivalents.

What is claimed is:

1. A preassembled surgical instrument, the preassembled surgical instrument comprising: an implant; a tulip connected to the implant; an extension connected to the tulip; an ini threadedly engaged with at least one of the tulip and the extension; and a first exchangeable pressure ring disposed at least partially between the implant and the tulip, wherein the first exchangeable pressure ring permits a first type of movement between the implant and the tulip; the first exchangeable pressure ring is exchangeable with a second exchangeable pressure ring; the second exchangeable pressure ring permits a second type of movement between the implant and the tulip; and the second type of movement is different than the first type of movement.

2. The preassembled surgical instrument of claim 1, comprising a breaker sleeve disposed around the extension and configured for breaking the extension off of the tulip at a predetermined breaking point.

3. The preassembled surgical instrument of claim 2, wherein the breaker sleeve is configured for breaking the extension off of the tulip extracorporeally.

4. The preassembled surgical instrument of claim 1, wherein the ini comprises a through hole configured to permit an implant driver to extend through the ini to a head of the implant.

5. The preassembled surgical instrument of claim 1, comprising an ini screwdriver configured to extend through the extension to drive the ini.

6. The preassembled surgical instrument of claim 5, comprising a T-handle with an integrated torque limiter configured for driving the implant driver.

7. The preassembled surgical instrument of claim 1, wherein the second type of movement includes substantially no movement between the tulip and the implant.

8. A surgical instrument, comprising: an implant; a tulip connected to the implant; an ini configured to engage the tulip; a tulip extension connected to the tulip; and an exchangeable pressure ring, wherein the exchangeable pressure ring is a first exchangeable pressure ring configured to permit a first type of movement between the implant and the tulip; a second exchangeable pressure ring may be exchanged with the first exchangeable ring; the second exchangeable pressure ring is configured to permit a second type of movement between the implant and the tulip; and, the second type of movement is different than the first type of movement.

9. The surgical instrument of claim 8, wherein the exchangeable pressure ring is a first exchangeable pressure ring configured to permit a first type of movement between the implant and the tulip; a second exchangeable pressure ring may be exchanged with the first exchangeable ring; and, the second exchangeable pressure ring is configured to fix the implant relative to the tulip.

10. The surgical instrument of claim 8, comprising:
a hollow extension shaft connected to the tulip extension at an end opposite from the tulip; and
a guide wire disposed in the extension shaft.

11. The surgical instrument of claim 10, wherein the guide wire is disposed in the ini and the implant.

12. The surgical instrument of claim 8, wherein the first exchangeable pressure ring and the second exchangeable pressure ring are exchangeable during an operation on a patient.

13. The surgical instrument of claim 8, wherein the first exchangeable pressure ring includes a predetermined breaking point to facilitate exchanging of the first exchangeable pressure ring.

14. The surgical instrument of claim 8, comprising a driver for driving the implant, wherein an aperture of the ini includes a diameter larger than a diameter of the implant driver such that the implant driver may be inserted through the ini to drive the implant.

15. The surgical instrument of claim 8, wherein the ini and the implant each include a polygonal socket and the polygonal socket of the ini includes a larger maximum diameter than a maximum diameter of the polygonal socket of the implant.

16. The surgical instrument of claim 8, comprising a breaking sleeve having a diameter larger than a maximum diameter of the tulip extension, wherein the breaking sleeve is configured for sliding over to the tulip extension to break the tulip extension off from the tulip extracorporeally at the predetermined break point.

17. The surgical instrument of claim 8, comprising a counterholder configured for preventing rotation of the tulip extension and the tulip if the ini and/or the implant is being driven.

18. The surgical instrument of claim 8, wherein the tulip, the tulip extension, and the extension shaft are formed as a single, unitary component.

* * * * *